United States Patent
Etienne-Cummings et al.

(10) Patent No.: US 7,164,967 B2
(45) Date of Patent: Jan. 16, 2007

(54) BIOMORPHIC RHYTHMIC MOVEMENT CONTROLLER

(75) Inventors: Ralph Etienne-Cummings, Baltimore, MD (US); M. Anthony Lewis, Mahomet, IL (US)

(73) Assignee: Iguana Robotics, Inc., Urbana, IL (US)

( * ) Notice: Subject to any disclaimer, the term of this patent is extended or adjusted under 35 U.S.C. 154(b) by 0 days.

(21) Appl. No.: 10/009,799

(22) PCT Filed: May 2, 2001

(86) PCT No.: PCT/US01/14231

§ 371 (c)(1),
(2), (4) Date: Oct. 30, 2002

(87) PCT Pub. No.: WO01/84279

PCT Pub. Date: Nov. 8, 2001

(65) Prior Publication Data

US 2003/0120385 A1 Jun. 26, 2003

Related U.S. Application Data

(60) Provisional application No. 60/201,748, filed on May 4, 2000.

(51) Int. Cl.
*G06F 19/00* (2006.01)

(52) U.S. Cl. .............. 700/245; 700/258; 600/557; 600/587; 600/595; 73/379.01; 623/16

(58) Field of Classification Search .......... 700/245, 700/253, 258; 318/568.11, 568.17; 901/23, 901/34; 701/23; 706/26
See application file for complete search history.

(56) References Cited

U.S. PATENT DOCUMENTS

| 5,355,435 A * | 10/1994 | DeYong et al. ............ 706/26 |
| 6,532,400 B1 * | 3/2003 | Jacobs .................... 700/245 |
| 6,741,911 B1 * | 5/2004 | Simmons ................ 700/245 |
| 2005/0065650 A1 * | 3/2005 | Lewis .................... 700/245 |

OTHER PUBLICATIONS

Giacomo indiveri, aVLSI-CPG for four legged robot, 1997, Internet, p. 1.*
Lewis et al., Toward biomorphic control using custom a VLSI CPG chips, no date, Internet, pp. 1-7.*

(Continued)

*Primary Examiner*—Thomas Black
*Assistant Examiner*—McDieunel Marc
(74) *Attorney, Agent, or Firm*—Whitham, Curtis, Christofferson & Cook, P.C.

(57) ABSTRACT

An artificial Central Pattern Generator (CPG) based on the naturally-occuring central pattern generator locomotor controller for walking, running, swimming, and flying animals may be constructed to be self-adaptive, by providing for the artificial CPG, which may be a chip, to tune its behavior based on sensory feedback. It is believed that this is the first instance of an adaptive CPG chip. Such a sensory feedback-using system with an artificial CPG may be used in mechanical applications such as a running robotic leg, in walking, flying and swimming machines, and in miniature and larger robots, and also in biological systems, such as a surrogate neural system for patients with spinal damage.

61 Claims, 8 Drawing Sheets

OTHER PUBLICATIONS

Billard et al., Biologically inspired neural controllers for motor control in a quadruped robot, 2000, IEEE, p. 1-5.*

Delcomyn et al., Architectures for biomimetic hexaped robot, 2000, Internet, p. 5-15.*

Inada et al., Behavior generation of bipedal robot using central pattern generator (CPG) (1st Report: CPG parameters searching method by genetic algorithm), 2003, IEEE, p. 2179-2184.*

Fraser, The biological neuron, Internet, Sept. 21, 1998, p. 1 of 1.*

* cited by examiner

BIOMORPHIC RHYTHMIC MOVEMENT CONTROLLER

RELATED APPLICATION

This is a PCT application claiming priority based on U.S. application No. 60/201,748 filed May 4, 2000, which is incorporated by reference herein.

STATEMENT REGARDING GOVERNMENT FUNDING

This invention was made under NSF grant number 9896362. The Government may have certain rights in this invention.

FIELD OF THE INVENTION

The invention generally relates to robotics and movement control, and more particularly, to rhythmic movement control systems that are sensitive and adaptive to the environment in which they are used.

BACKGROUND OF THE INVENTION

Basic rhythmic movements in animals are generated by a network of neurons in the spinal cord called the Central Pattern Generator ("CPG"). Walking, running, swimming, and flying animals have a biological locomotor controller system based on a CPG, which is an autonomous neural circuit generating sustained oscillations needed for locomotion. Naturally-occurring CPGs have been studied and are beginning to be understood. Scientists have studied these naturally-occurring biological CPG systems and, in the early 1900s, articulated the basic notion of such an oscillation-generating autonomous neural circuit for locomotion. T. G. Brown, "On the nature of the fundamental activity of the nervous centres; together with an analysis of the conditioning of the rhythmic activity in progression, and a theory of the evolution of function in the nervous system," J. Physiol., vol. 48, pp. 18–46 (1914).

An autonomous system of neurons can generate a rhythmic pattern of neuronal discharge that can drive muscles in a fashion similar to that seen during normal locomotion. Locomotor CPGs are autonomous in that they can operate without input from higher centers or from sensors. Under normal conditions, however, these CPGs make extensive use of sensory feedback from the muscles and skin, as well as descending input. A. H. Cohen, S. Rossignol and S. Grillner, Neural Control of Rhythmic Movements in Vertebrates (Wiley & Sons, 1988). Furthermore, the CPG transmits information upward to modulate higher centers as well as to the periphery to modulate incoming sensory information.

The CPG is most often thought of as a collection of distributed elements. For example, in the lamprey (a relatively simple fish-like animal), small, isolated portions of the spinal cord can generate sustained oscillations. When the spinal cord is intact, these small elements coordinate their patterns of activity with their neighbors and over long distances.

It is well known that sensory input can modulate the activity of naturally-occurring, biological CPGs. Modulation of the CPG by sensory input can be seen quite clearly in the adjusting of the phase of the CPG. For example, as a walking cat pushes its leg back, sensors in the leg muscles detect stretching. These sensors (called stretch receptors) signal this stretch to the nervous system. Their firing initiates the next phase of the CPG causing the leg to transition from stance to swing phase.

After some study of naturally-occurring biological CPG systems, scientists modeled CPGs as systems of coupled non-linear oscillators. In the early 1980s Cohen and colleagues introduced a model of the lamprey CPG using a system of phase-coupled oscillators. A. H. Cohen, P. J. Holmes and R. H. Rand, "The nature of the coupling between segmental oscillators of the lamprey spinal generator for locomotion: A mathematical model," J. Math. Biol., vol. 13, pp. 345–369 (1982). Later, a model called Adaptive Ring Rules (ARR) based on ideas in Cohen et al.'s and related work was extended for use in robot control. M. A. Lewis, Self-organization of Locomotory Controllers in Robots and Animals, Ph.D. dissertation, Dept. of Electrical Engineering, Univ. of Southern Calif., Los Angeles (1996). An ARR is a model of a non-linear oscillator at a behavioral level. Complex enough to drive a robot, an ARR model also allows relatively easy implementation of learning rules.

Certain conventional non-biological (i.e., modeled) CPG-type chips and circuits have been developed. For example, Still reported on a VLSI implementation similar to a CPG circuit used to drive a small robot. S. Still, Presentation at Neurobots Workshop, NIPS*87, Breckenridge, Colo., U.S.A. (1998); S. Still and M. W. Tilden, "Controller for a four legged walking machine, in Neuromorphic Systems: Engineering Silicon from Neurobiology, Eds: L. S. Smith and A. Hamilton (World Scientific, Singapore), pp. 138–148 (1998). Still et al.'s circuit captured some basic ideas of a CPG, and Still's group demonstrated rudimentary control of a walking machine. However, Still's system has no motoneuron output stage, and cannot respond to or adapt based on sensory input.

Ryckebusch and colleagues created a VLSI CPG chip based on observations in the thoracic circuits controlling locomotion in locusts. S. Ryckebusch, M. Wehr, and G. Laurent, "Distinct Rhythmic Locomotor Patterns Can Be Generated by a Simple Adaptive Neural Circuit: Biology, Simulation and VLSI Implementation," J. of Comp. Neuro., vol. 1, pp. 339–358 (1994). The resulting VLSI chip was used as a fast simulation tool to explore understanding of the biological system. Their system is not a robotic system and cannot respond to or use feedback from sensors.

DeWeerth and colleagues have captured certain neural dynamics on a detailed level. G. Patel, J. Holleman, and S. DeWeerth, "Analog VLSI Model of Intersegmental Coordination with Nearest-Neighbor Coupling," in Adv. Neural Information Processing, vol. 10, pp. 719–725 (1998). This system of DeWeerth's cannot easily be applied to control a robot, primarily because parameter sensitivity makes such circuits difficult to tune. To address this difficulty, DeWeerth et al. more recently have implemented neurons that self-adapt their firing-rate. M. Simoni, and S. DeWeerth, "Adaptation in a VLSI Model of a Neuron," in: Trans. Circuits and Systems II, vol. 46, no. 7, pp. 967–970 (1999). The adapted DeWeerth system, however, is not adaptive and does not use external inputs from sensors.

U.S. Pat. No. 5,124,918, entitled "Neural-based autonomous robotic system" to Beer et al., teaches a system for controlling a walking robot using a rhythmic signal used to coordinate locomotion with multiple legs. Beer et al.'s neural-based approach, using software, is relatively basic and does not teach, for example, VLSI implementation, self-adaptation to an environment, low-power compact implementation using one chip, or silicon learning.

In recent years, robotics has been developing in many aspects, of which some have been mentioned above. Also, other challenges have been identified and are being studied in robotics, such as the miniaturization of walking, running, and flying robots, increasing the real-time adaptability of robots to the environment, and the creation of mass-market consumer devices. With these new robotics technologies come demands for smaller, lower-cost, more power-efficient, more adaptive controllers, and, correspondingly, computational support.

Robotics has largely relied for computational support on microprocessor-based technology. Such systems have limitations, such as being unable to provide self-adaptive features.

Not necessarily connected with robotics technologies, a field of neuromorphic engineering developed. Neuromorphic engineering uses principles of biological information processing to address real-world problems, constructing neuromorphic systems from silicon, the physics of which in many ways resembles the biophysics of the nervous system. Neuromorphic engineering to date mostly has concentrated on sensory processing, for example, the construction of silicon retinas or silicon cochleas.

Thus, interesting and exciting advances have been made in the thus-far relatively separate technologies of robotics and neuromorphic engineering. However, work remains to be done to practically bring together these technologies. Conventional robotics and related systems are non-adaptive to their environments, and theoretically the potential exists for huge advances in the direction of increased adaptiveness to the environment. Advanced robotics systems, control of mechanical limbs, control of biological limbs, rhythmic movement in biological systems, have been desired, such as increased responsiveness and relatedness to the environment.

SUMMARY OF THE INVENTION

After investigating and considering how to make a modeled, non-biological CPG self-adapt, the present inventors arrived at this invention, in which a non-biological CPG tunes itself with sensory feedback The present invention provides miniature and non-miniature robotics systems, modeled non-biological systems that may be used in biological applications, chips, movement machines, and other systems that receive sensory input from, and are adaptive to, an environment in which they are operating. For example, the present invention applies ARR theory in designing such a man-made CPG chip. (Man-made CPG chips, systems and the like are referred to herein as "non-biological" and/or "CPG-based".) It is a basic object of the present invention to construct non-biological systems mimicking features of CPGs that occur in nature. ("Biological CPG" is used herein as a shortened way to refer to a CPG that occurs in nature.)

It is a further object of the present invention to elucidate practical applications in which non-biological CPG systems may be used. Examples of applications for non-biological CPG systems include use in biological systems (such as the human body) as well as non-biological systems (such as robots, movement machines, breathing controllers, and the like). It is a further object of the present invention to provide for controlling one or more mechanical limbs via a CPG-based system, and to provide for controlling rhythmic movement in a biological system via a CPG-based system.

A further object of the invention is to elucidate ways in which a modeled CPG system may be made adaptive and responsive to the environment in which it is used. As an important example, the invention provides advanced robotics systems and autonomous movement devices (including breathing controllers, running devices, swimming devices, flying devices, and other devices) with sophisticated responsiveness and adaptability to the environments in which they are used.

In order to accomplish these and other objects of the invention, the present invention in a preferred embodiment provides a CPG-based system, such as a CPG-based system for controlling at least one mechanical limb, comprising at least one mechanical limb and a non-biological CPG that generates commands for controlling the at least one mechanical limb wherein commands are a function of sensory feedback. The invention provides a CPG-based system for controlling a biological system for rhythmic movement, comprising: (1) an interface with a biological system that can provide sensory feedback from said biological system, and (2) a non-biological CPG that generates commands for controlling the biological system wherein commands are a function of sensory feedback.

In a particularly preferred embodiment, the invention provides for the CPG-based system to include a system for phase adjustment of the CPG based on a sensory trigger in or derived from sensory feedback. In another particularly preferred embodiment, the CPG-based system may include a system for phase adjustment of the central pattern generator based on at least one sensory trigger in or derived from sensory feedback; and a system for controlling firing frequency of motoneurons as a function of the sensory feedback or the sensory trigger.

In a further embodiment, the invention provides for the CPG-based system to include at least one memory device. In a preferred embodiment of the invention, the memory device controls adaptation of output from the CPG. In a preferred embodiment of the invention, the output includes integrate-and-fire neurons.

The invention also provides for another preferred embodiment in which the CPG-based system is at least one chip, and in another preferred embodiment, multiple chips. In a particularly preferred embodiment, the inventive chip contains electronic analogues of biological neurons, synapses and time-constraints. In another particularly preferred embodiment, the inventive chip includes dynamic memories and phase modulators. Another preferred embodiment provided by the invention is a system including at least one chip in which components are integrated with hardwired or programmable circuits.

The invention in another preferred embodiment provides for the CPG-based system to be a non-linear oscillator including electronic analogues of biological neurons, synapses and time-constraints, dynamic memories and phase modulators. The invention in a preferred embodiment provides a CPG-based system wherein the CPG is a distributed system of at least two non-linear oscillators. In a further inventive embodiment, the invention provides for the distributed system to include at least one neuron phasically coupled to a neuron or a sensory input. In another inventive embodiment, the distributed system includes at least two neurons phasically coupled to each other, to another neuron, or to a sensory input. The invention provides in another embodiment for phasic coupling that is in-phase, 180 degrees out of phase, or any number of degrees out of phase. In a particularly preferred embodiment, the invention provides phasic coupling based on rhythmic movement application. In an especially preferred embodiment, the invention provides for including a phase control circuit. Where phasically coupled nuerons are used, the invention provides in another embodiment for including at least one integrate-and-fire spiking motoneuron driven by the phasically coupled neurons.

The invention also provides in another embodiment for including at least one muscle in the CPG-based system.

A particularly preferred embodiment of the present invention provides a robot.

The invention in a further embodiment provides for the CPG-based system to include a CPG chip and at least one biological neuron. The invention also provides an embodiment in which a CPG-based system includes at least one sensor for collecting sensory feedback. In a particularly preferred embodiment, the CPG-based system includes a system for phase adjustment of the central pattern generator based on at least one sensory trigger in the received sensory feedback. The invention provides an embodiment in which sensory feedback is received from a mechanical limb or from a biological limb. The invention also provides an embodiment wherein the sensory feedback is received from a sensing modality.

The invention also provides methods for controlling a mechanical or biological system for rhythmic movement, such as methods comprising: (A) measuring sensory feedback to obtain measured sensory feedback; (B) processing the measured sensory feedback to obtain data for a plurality of designated parameters; and (C) via a CPG-based system, applying a set of rules to the obtained data to generate at least one signal for commanding the limb or biological system for rhythmic movement, wherein the CPG-based system comprises a circuit that mimics a biological CPG. In a preferred embodiment, such an inventive method includes, via the CPG-based system, applying the generated signal to command the limb or biological system for rhythmic movement. The invention also provides for a method wherein the CPG system comprises a circuit comprising at least two coupled non-linear oscillators.

The invention also provides for further embodiments that are robotics systems, such as a robotics system comprising: (a) a CPG-based system that mimics a biological central pattern generator; and (b) at least one sensory device. The invention also provides that in a particularly preferred embodiment of the robotics system, the CPG-based system receives sensory input from the at least one sensory device.

The invention also provides autonomous movement devices, such as an autonomous movement device for providing rhythmic control, wherein the autonomous device comprise a non-biological CPG that generates rhythmic control commands wherein commands are a function of sensory feedback. The invention in a further embodiment provides for the autonomous movement device to include at least one mechanical limb. In another embodiment, the invention provides that the limb is a leg, arm, wing or appendage for swimming. In some embodiments of the invention, at least two limbs are included. The invention in other embodiments provides a breathing controller, a pacemaker, and a running device.

The invention also provides a non-biological CPG comprising a memory device; and a system for manipulating neural phasic relationships.

Further, the invention provides a method for modifying a continuous waveform provided by a non-biological CPG, comprising the steps of: (A) provision of a continuous waveform by a non-biological CPG; (B) provision of sensory feedback to the non-biological CPG; (C) rule-application by the non-biological CPG to the sensory feedback; (D) based on the rule-application, determination by the non-biological CPG to modify or maintain the continuous wave form. In a particularly preferred embodiment of such a method for modifying a continuous waveform, the invention provides for the non-biological CPG to modify the wave form. In another embodiment that is particularly preferred, the invention provides for the the rule-application to be the application of adaptive ring rules.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
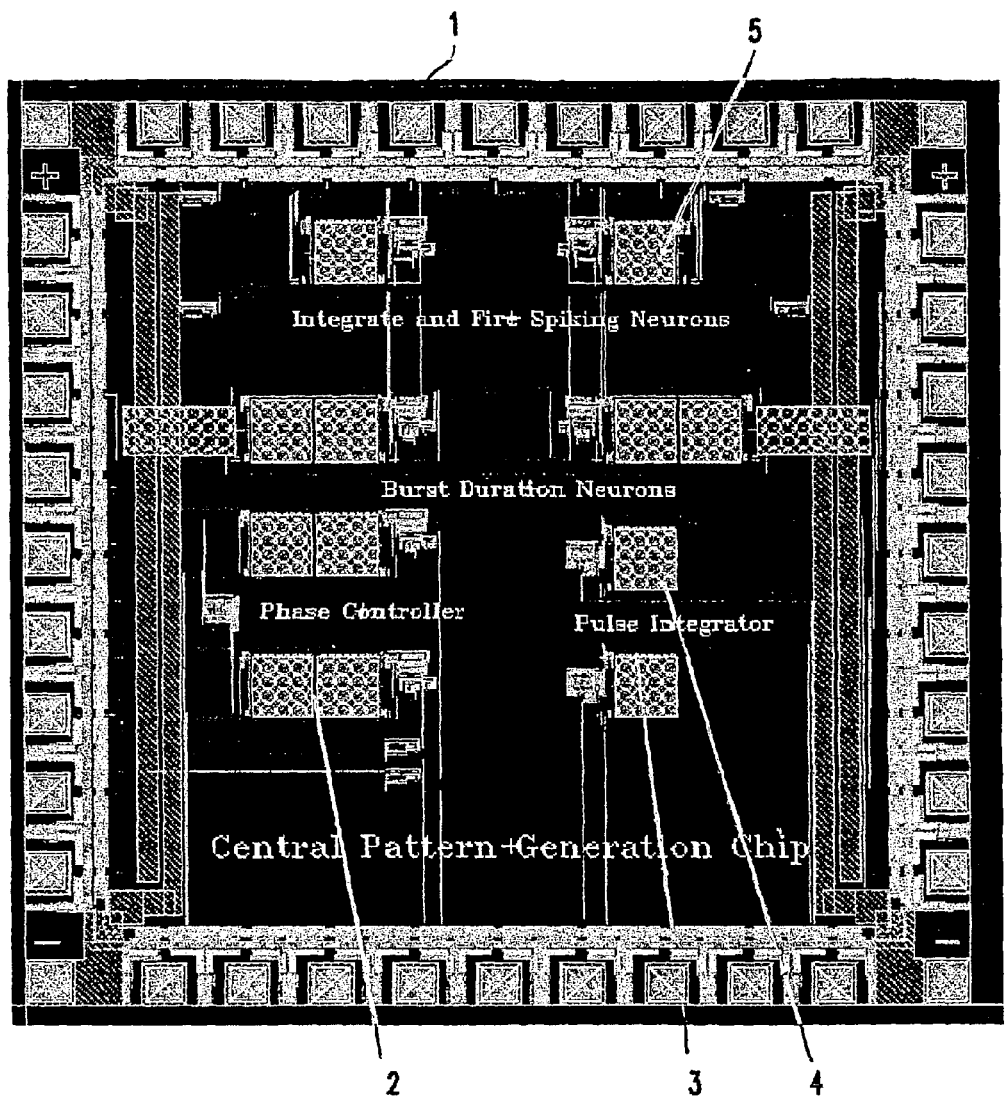
FIG. 1 depicts the layout of an example of a CPG chip according to the invention.

The invention provides a non-biological CPG-based system which is adaptive to the environment in which it is used. To be adaptive, the CPG system receives sensory feedback from the environment and acts based on the received sensory feedback. In one preferred embodiment, the invention provides a CPG-based system that controls one or more mechanical limbs. In another preferred embodiment, the invention uses a CPG-based system for controlling rhythmic movement in a biological system, such as one or more biological limbs or structures. Walking, swimming, flying, hopping and breathing machines, by way of non-limiting example, may be made using the invention. In the non-biological CPG-based system, a non-biological CPG generates commands that are a function of sensory feedback.

"Sensory feedback" as mentioned in the present invention refers to any sensory information that is or is processible into information that is recognizable by a non-biological CPG. Sensory feedback may be from a mechanical source (such as a mechanical limb, camera or other artificial vision, artificial audition, artificial muscle sensors, etc.) or a biological system (such as neural signals from muscles, neural signals from brain regions, etc.). In a preferred embodiment of the present invention, sensory feedback from multiple sources is provided to a non-biological CPG.

For obtaining the sensory feedback from a mechanical source, one or more sensors may be provided for collecting sensory feedback. The sensor may receive the sensory feedback from any sensing modality. A sensor for use in the invention is not particularly limited and maybe artificial vision, artificial audition, artificial muscle sensors, or sensors for measuring any natural or environmental condition (such as weather, air quality or content (e.g., acidity), presence of chemicals, fire, temperature, pressure, lighting conditions, gunfire, microwaves, optical information, etc.), contact sensors, etc.

When a sensor is used, the positioning of the sensor is not particularly limited with regard to the non-biological CPG, and the sensor and the CPG may be disposed in any manner in which they are in communication with each other, directly or indirectly. The manner in which communication between a sensor and a non-biological CPG may be established, directly or indirectly, is not particularly limited, and the sensor and non-biological CPG may be connected electrically such as by being wired to each other. In an example of a CPG chip according to the invention shown in FIG. 1, all the components are individually accessible such that they can be connected with off-chip wiring to realize any desired circuit. Neural CPG circuits can be integrated with completely hardwired or programmable circuits. The sensor and the CPG chip may be connected non-electrically, such as optically, by a wireless connection, by infra-red, chemically, or connected electrically and chemically.

The non-biological CPG and the sensor communicate in a language understood by both, e.g., spike-coded, digital interface, analog interface, etc. The language may be selected based on the non-biological CPG and the sensor being used. One skilled in the art is familiar with establishing an interface according to the components to be put in communication with each other, such as the non-biological CPG and the sensor.

In a preferred embodiment, a sensor may be used in relatively close proximity to the non-biological CPG, for providing information about the immediate environment of a CPG-based system according to the invention, or of a patient in which a CPG-based system is operating.

However, it will be appreciated that in some applications it may be advantageous to operate with a substantial distance between a sensor and a non-biological CPG. For example, a sensor may be placed on or in an object or person who may need rescuing, to be used, if needed, in cooperation with a moving rescuer device comprising a non-biological CPG.

A non-biological CPG for use in the present invention is at least one circuit that is pattern-generating and further is configured to generate commands (such as self-adapting) as a function of sensory feedback. The pattern-generating of the non-biological CPG in a most preferred example may be provision of continuous waveforms, with the waveforms being a function of one or more waveform parameters. A waveform parameter may be any parameter that accomplishes an adjustment associated with a predetermined feature of movement, and may depend on the movement. For example, in the case of two-legged movement, waveform parameters may include "center of stride", "left/right" adjustment, "length of stride", "frequency of stride", "height", etc. Those skilled in the art are familiar with generally selecting a wave-form for a non-biological CPG to match and thus provide a particular desired motion, such as selecting a waveform to provide a running motion with a certain center, length and frequency of stride. In the present invention, it is preferred that the non-biological CPG be configured to provide a variety of continuous waveforms and to easily self-reset from one waveform being generated to another waveform.

Preferably, a non-biological CPG for use in the invention is one configured with safeguarding to only permit generation of waveforms within the capabilities and performance specifications of the system in which it is used, such as not permitting hyper-extension, not generating a wave-form that would overstretch or otherwise harm a patient in which it is implanted, etc. On the other hand, preferably a non-biological CPG for use in the invention within such a safeguarded range has a rich array of waveforms, to provide fine movement details.

To be suitable for use in the present invention, the non-biological CPG is configured to generate commands as a function of sensory feedback. For example, as seen with reference to FIGS. 7(a) and 8, a CPG chip 1 which is a preferred embodiment of the invention may be used in a biological system such as a human patient. The CPG chip 1 may receive sensory feedback from neural signals from muscles 6, artificial vision 7, artificial audition 8, artificial muscle sensors 9, and neural signals from brain regions 10. The CPG chip 1 may issue commands 100 to muscles and limbs 11. A dotted line shows direct and indirect influence 110 of the sensory feedback.

Figure 7A:
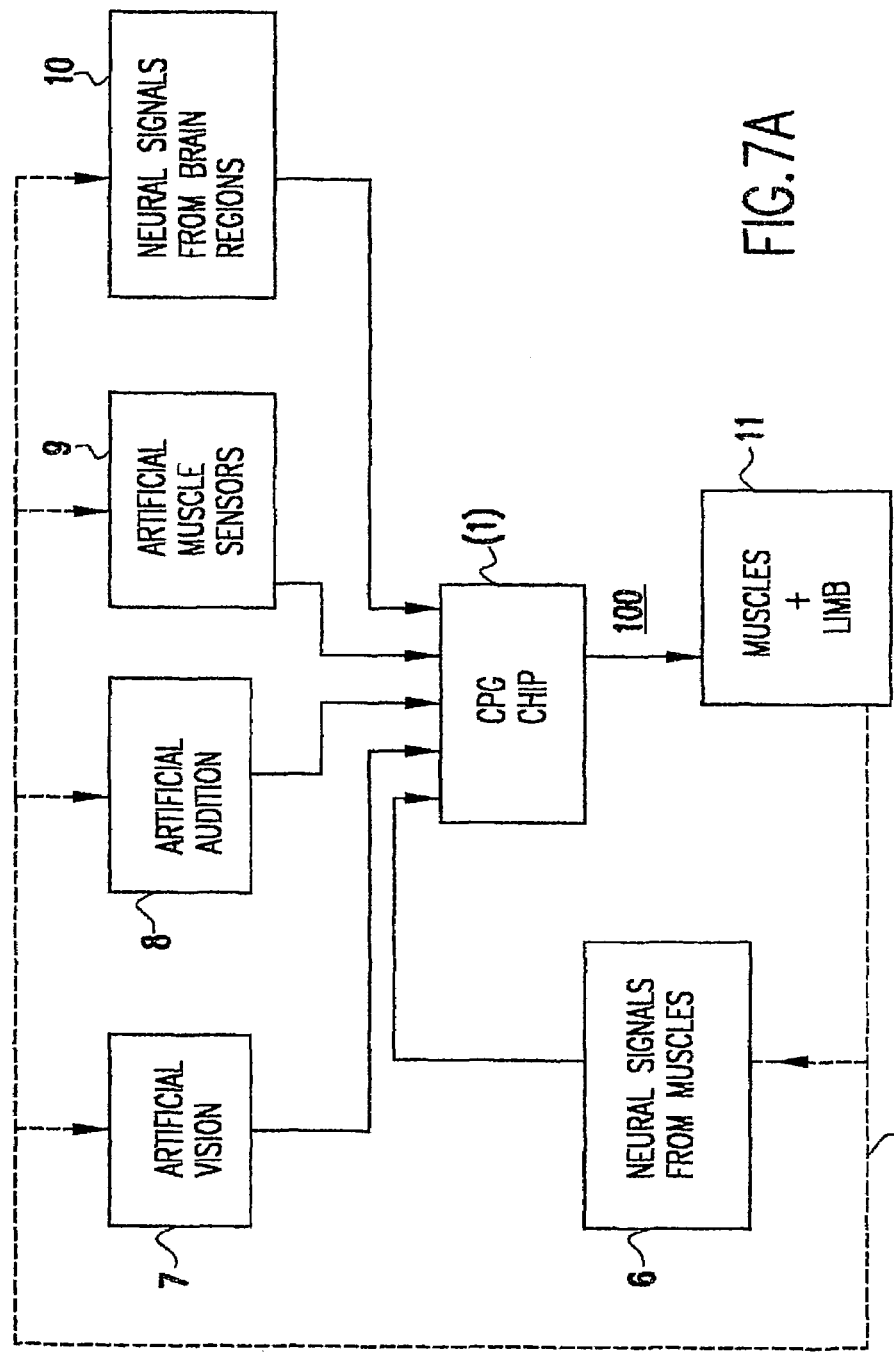
FIG. 7(a) is a flow chart showing an exemplary relationship of a CPG chip according to the invention and sensory input.
Figure 8:
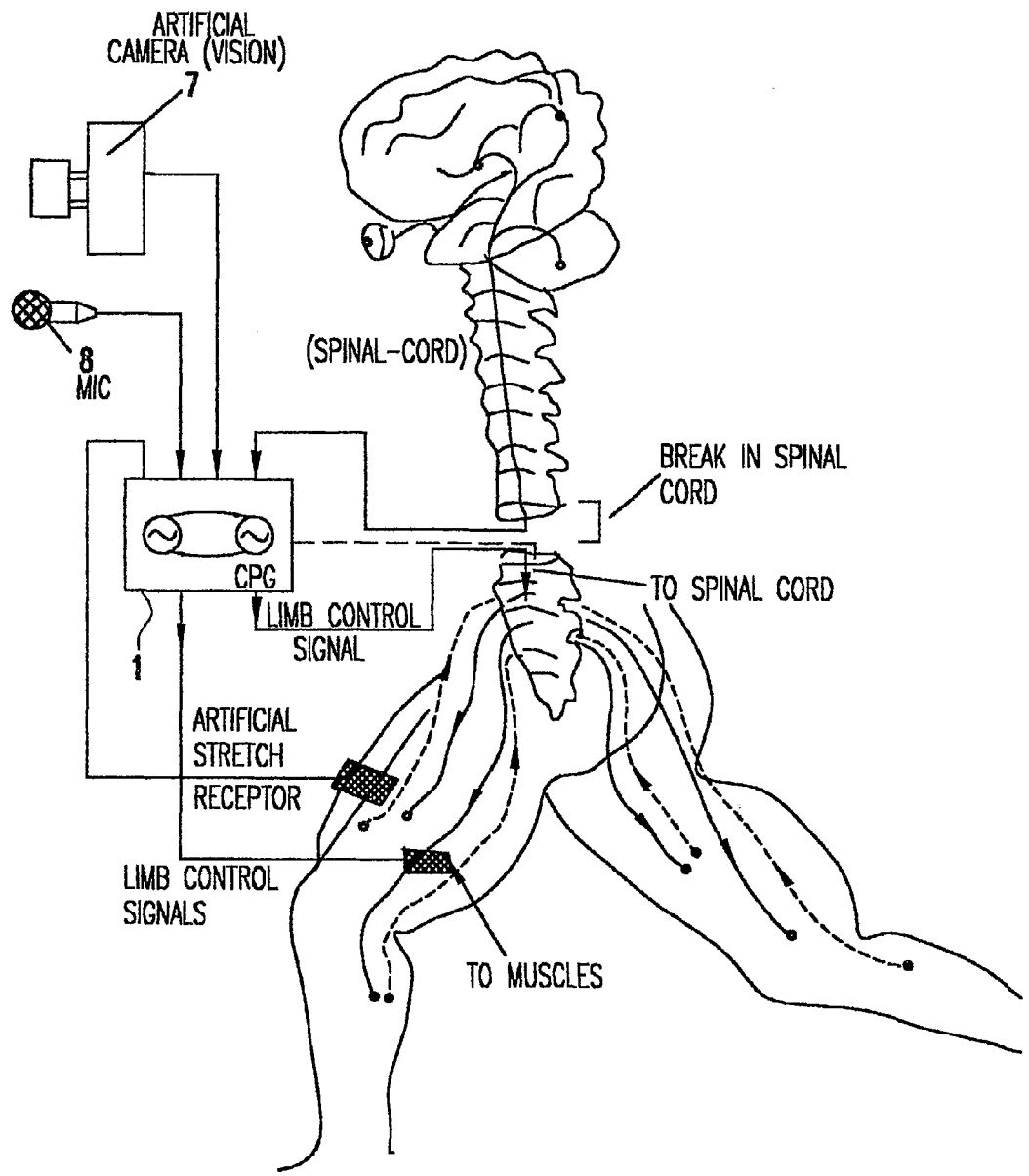
FIG. 8 is a cross-section view showing use of a CPG chip according to the invention in a human patient with a damaged spinal cord.

When a CPG chip is used in a biological system, such as shown in FIGS. 7A and 8 by way of example, an interface between the CPG chip and the biological system is provided. The interface is one that can provide sensory feedback from the biological system to the CPG chip in the form of electrical signals. Measurement of electrical activity in neurons is known in neurophysiology and such measurement techniques may be used in the invention. The activity of neurons can be sensed using electronic probes that measure the electrical discharge of the cells. These signals are usually small, and may be amplified so that they can be provided to the CPG chip as voltage spikes. The interface with the biological system may be any interface capable of providing voltage spikes to the CPG, such as chronically implanted micro electrodes that may be used to measure the electrical activity of neurons in the muscles, spine or brain. The microprobes may be connected, with thin wires, to a pre-amplifier chip that magnifies the signals from millivolts to volts. The magnified signals may be presented to the CPG chip as pulses to the synapses.

The non-biological CPG of the present invention comprises any biologically plausible circuit or circuits for controlling motor systems. The definition of a non-biological CPG in terms of biological plausibility for controlling motor systems is not intended to limit a non-biological CPG according to the invention to motor systems applications.

An example of a non-biological CPG for use in the invention is a memory device combined with a system for manipulating neural phasic relationships, such as a non-biological CPG that maintains a continuous wave-form and self-adapts the waveform based on sensory feedback.

As has been said, the non-biological CPG for use in the present invention is one that generates commands as a function of sensory feedback. In a preferred embodiment of the present invention, to generate such commands, the sensory feedback which consists of electrical signals is evaluated to determine what, if any, effect the sensory feedback is to have on the wave form being provided. The non-biological CPG may be programed to recognize one or more sensory triggers in the sensory feedback, and for each particular sensory trigger found, to respond according to a predetermined rule. For such evaluation of the sensory feedback, programming for cyclic readjustment of signals, such as ARR, may be applied. ARR programming preferably is used for such evaluation of the sensory feedback. Sufficient memory and/or data storage are provided to support evaluation of the sensory feedback.

By way of a non-limiting example, a non-biological CPG according to the present invention may be programmed to recognize in sensory feedback from a visual sensor, a certain pattern as a hole, to treat the hole as a certain sensory trigger, and therefore to adjust the waveform in progress according to a certain pre-determined rule or set of pre-determined rules.

Methods of evaluating and characterizing sensory feedback known to those skilled in the art may be used in the present invention, such as known methods of characterizing data from an artificial vision system such as a camera, known methods of characterizing data from an artificial audition system, etc.

A non-limiting example of a CPG-based system according to the invention is as follows, discussed with reference to FIGS. 7(a), 7(b) and 8. When the system is started, the CPG chip begins running an initial continuous waveform. A sensor (such as artificial vision 7 in FIGS. 7(a) and 8) collects sensory information and, directly or indirectly (such as after processing to be readable by the CPG chip) sends sensory feedback to the CPG chip. The sensory feedback may be sent from the sensor to the CPG chip directly such as by a circuit. Sensory feedback information is transmitted for receipt by the CPG chip in the form of electrical signals.

Figure 7B:
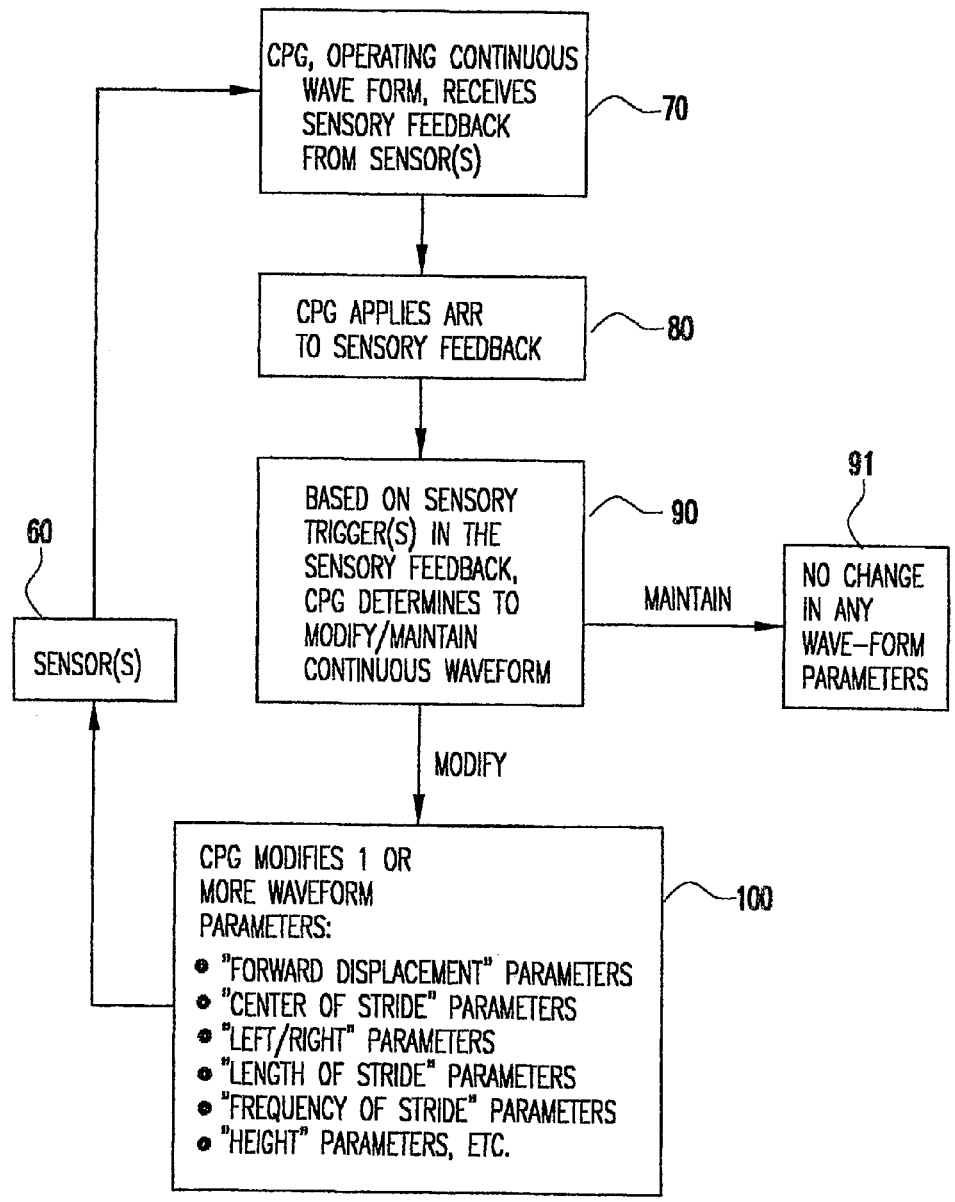
FIG. 7(b) is a flow chart showing a simple example of processing that occurs for information collected by a sensor according to the invention.

As shown on FIG. 7(b), in a preferred embodiment of the invention, a CPG chip receives sensory feedback from one or more sensors 60. The CPG chip receives 70 the sensory feedback in the form of electrical signals, and then applies ARR 80 relating to predetermined sensory triggers to the sensory feedback. Based on sensory triggers in the sensory feedback, the CPG chip determines 90 whether to modify or maintain the continuous waveform that is in progress. If the CPG chip determines to maintain 91 the waveform in progress, no change to any waveform parameter is commanded. If the CPG chip determines to modify 100 the waveform in progress, the CPG chip alters one or more waveform parameters, such as, in this example, "forward displacement", "center of stride", "left/right", "length of stride", "frequency of stride", "height", etc.

Most preferably, the CPG applies ARR to the sensory feedback in as short a time as possible. For example, if a sensor in a walking machine provides sensory feedback indicating a hole, desirably such sensory feedback is processed and acted on before the walking machine travels into the hole.

With reference to FIG. 7(b), information resulting from modification by the CPG 100 of 1 or more waveform parameters is sent to the sensors 60. In FIG. 7(b), by way of example, sensory feedback is shown with regard to sensors 60, but it will be appreciated that the sensors 60 are only an example of a source of sensory feedback and may instead be a biological system, or a combination of sensors and a biological system.

As may be appreciated with reference to FIGS. 7(a) and 7(b), based on sensory feedback, a CPG-based system according to the invention self-adapts. The self-adapting is not particularly limited, and may comprise any command (such as a waveform phase adjustment or other action that the CPG undertakes) that is a function of sensory feedback. In a preferred example, the self-adapting comprises a system for phase adjustment of the CPG based on a sensory trigger in or derived from sensory feedback, or a system for controlling firing frequency of motoneurons as a function of the sensory feedback or the sensory trigger.

In a preferred embodiment of the invention, at least one memory device is used. Preferably, the memory device is one that controls adaptation of output such as output parameters from the CPG. The memory device may be a short-term memory device. Preferably, a high level of abstraction is used to more easily implement on-chip learning. Systems based on numerous inter-related parameters are avoided because in such systems it is not apparent how learning at the level of behavior can be coupled to low level parameter changes. The memory device may be a dynamic analog memory, or a digital memory device.

A CPG-based system according to the invention is not particularly limited in its form, and may be in the form of one or more chips, a robot, a movement machine (such as a walking, running, swimming, flying or breathing machine), a biological system etc.

An example of a preferred embodiment of the invention is a CPG chip 1 as shown in FIGS. 1, 7(a) and 8. As seen with reference to FIG. 1, the CPG chip 1 includes phase controller 2 and pulse integrator 3. Burst duration neurons 4 and integrate-and-fire spiking neurons 5 are provided on CPG chip 1. A schematic for an integrate-and-fire spiking neuron 5 is shown in FIG. 2.

Figure 2:
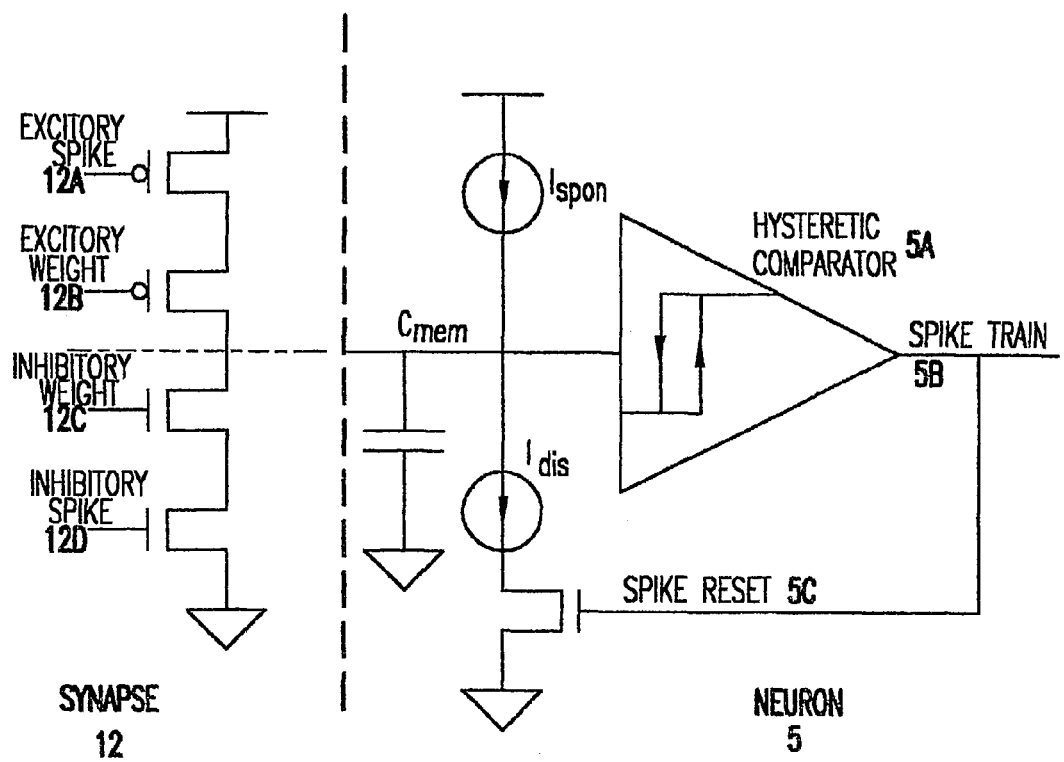
FIG. 2 is a schematic of an example of an integrate-and-fire motoneuron and synapse according to the invention.

In FIG. 2, on the right-hand side, hysteretic comparator 5a, spike train 5b and spike reset 5c of neuron 5 are shown. The left-hand side of FIG. 2 shows the schematic of the synapse 12 for neuron 5. Excitory spike 12a and excitory weight 12b, and inhibitory weight 12c and inhibitory spike 12d, are shown for synapse 12.

A chip used in a CPG-based system according to the invention may include dynamic memories and phase modulators. A CPG chip according to the present invention may be integrated with hardwired or programmable circuits, or may be used in any other form. In FIG. 1, the CPG chip is shown with each component wired to pins to facilitate the prototyping of oscillator circuits.

In a preferred embodiment of the invention, the CPG-based system is a non-linear oscillator based on the CPG of a biological organism. In a system comprising a non-linear oscillator, the system is non-linear and preferably includes a chip using non-linear elements, to provide a coupled system of non-linear elements, without linearizing the system. When a non-linear oscillator is used, because linearization is not used, instead principles from biological systems are used, which can be implemented easily with low-power integrated circuits, to provide a compact system.

The system may include electronic analogues of biological neurons, synapses and time-constraints. FIG. 2 depicts some examples of such electronic analogues.

Figure 3:
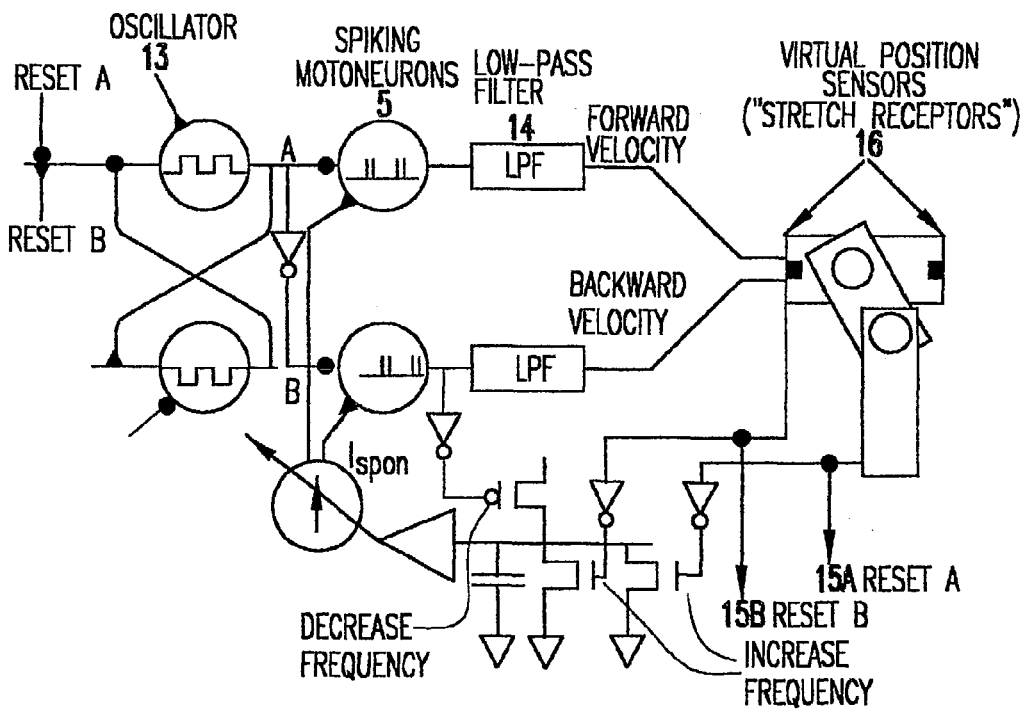
FIG. 3 is an example of a circuit diagram which is according to the invention and adaptively controls dynamics of a limb, by a neural non-biological CPG with learning capabilities.

The CPG-based system of the invention maybe a distributed system of at least two non-linear oscillators, of which FIG. 3 is an example. The circuit of FIG. 3 adaptively controls dynamics of a limb, by a neural non-biological CPG with learning capabilities. Other distributed systems of at least two non-linear oscillators may be used in the invention. Such a distributed system may include at least one neuron phasically coupled to a neuron or a sensory input. Preferably, the distributed system includes two or more neurons phasically coupled to each other, to another neuron, or to a sensory input.

The phasic coupling used in the invention may be in-phase, 180 degrees out of phase, or any amount out-of-phase. The phasic coupling may be selected based on desired end-use application such as a particular rhythmic movement. When an integrate-and-fire spiking motoneuron is used, a preferred integrate-and-fire spiking motoneuron is one driven by phasically coupled neurons. The phasic coupling feature may be provided as a phase control circuit, such as phase controller 2 in FIG. 1. Phase control circuits and phasic coupling are known to those skilled in the art.

The inventive CPG-based system may include one or more mechanical or biological limbs, examples of which are seen in FIGS. 7(a) and 8. The inventive CPG-based system is not limited to limbs, and in the case of biological systems, may include any biological system for rhythmic movement, in which case FIGS. 7(a) and 8 still are relevant, but replacing reference to a limb with that of an organ or other component of the body.

The CPG-based system according to the invention is especially suited for use in a biological system, such as the human body or an animal. In such an application, the CPG-based system may include one or more muscles, biological neurons, etc.

Above the invention has been discussed with regard to FIG. 1, showing a single CPG chip. It will be appreciated that FIG. 1 is an example and that the invention may be practiced using two or more chips. When multiple chips are used for constructing a CPG-based system according to the invention, those chips may be electrically connected as is known to those skilled in the art.

The invention also may be practiced by constructing a robot, such as a robot comprising one or more CPG chips according to FIG. 1. For making a robot according to the invention, a CPG-based system that mimics a biological CPG (such as a chip like that of FIG. 1) may be electrically connected with one or more sensors, and further may be connected with one or more memory devices. The memory device preferably is programmed with a set of adaptive ring rules relating to predetermined triggers that may be found in the sensory feedback from the particular sensors that are being used.

In another preferred embodiment, the invention provides a method for controlling a mechanical limb or biological system for rhythmic movement, by (A) measuring sensory feedback; (B) processing the measured sensory feedback to obtain data for at least one designated parameter; and (C) via a CPG-based system, applying a set of rules to the obtained data to generate at least one signal for commanding the limb or biological system for rhythmic movement. The processing may be to obtain data for a plurality of designated parameters, or, in a most simple example, to obtain data for one parameter. The CPG-based system used may be any system comprising a circuit that mimics a biological CPG. Such an inventive method preferably includes a further step of, via the CPG-based system, applying the generated signal to command the limb or biological system for rhythmic movement. For practicing such a method, preferably the CPG-based system comprises a circuit comprising at least two coupled non-linear oscillators.

In another preferred embodiment, the invention may be used to construct an autonomous movement device for providing rhythmic control. Such a device is constructed starting with a non-biological CPG that generates rhythmic control commands that are a function of sensory feedback, to which is added one or more movement components, such as one, two or more mechanical limbs, which may be a leg, arm, wing or appendage for swimming, or other limb. Examples of such a movement device maybe a running device, a flying device, a hopping device, a jumping device, a walker, a breathing controller or a pacemaker.

It will be appreciated that the uses of the present invention are not particularly limited, and examples may be biological and medical applications, movement and transportation applications, rescue applications, space exploration, toys, etc. However, such examples of uses of the present invention are not intended to be limiting.

As an example of a biological or medical application, the present invention in a particularly preferred embodiment may be used in treating patients with spinal total or partial spinal damage, such as by providing a spinal neural stimulator for paraplegics with a transected or crushed spinal cord. A chip according to the invention may be used to stimulate nerve cells that are responsible for walking. Such a chip outputs signals that are compatible with biological neural circuits.

Another preferred use of the present invention is to provide a chip that may control a leg vehicle (such as that of Iguana Robotics, Inc., PowerBoots technology) that assists the normal process of running, such that individuals can run faster, longer, jump higher while carrying more weight. Such a leg vehicle has applications in both civilian and military arenas. The adaptive properties of a control system according to the present invention allows a leg vehicle such as PowerBoot to "learn" the individual dynamics of the user and continuously fine-tune itself to optimize running efficiency, speed and power source lifetime. In addition, using the present invention in a leg vehicle may decrease the stress placed on the user by allowing the user to also modify the behavior of the controller through direct inputs.

It will be appreciated that uses of the invention in biological or medical applications are not necessarily limited to those in which a biological CPG was or is operating (such as for locomotion control) but also may be extended to uses in which a biological CPG may not have been involved, such as timed-release and other drug delivery (such as in the context of stimulating nerves). For example, a non-biological CPG system according to the invention may be implanted in the brain or spinal cord for accomplishing drug delivery. Also, the invention may be used in neuro-stimulation applications, for controlling epilepsy, and for chemical-sensing in a patient.

Another preferred embodiment of the invention uses a non-biological CPG chip as a control system for a robot, such as walking robot. In a particularly preferred embodiment, the robot can navigate rough terrain. For navigating such terrain, a multi-pedal walking machine may be used, with a controlling comprising a non-biological CPG chip that coordinates the limbs and adapt their behaviors based on the environment. With visual inputs, the robots can use adaptive CPG chips to run and hurdle obstacles at high speeds.

The present invention in another preferred embodiment is used in medical and biological applications, such as an implantable, neurologically compatible neural surrogate for a paralyzed individual. Such a neural surrogate according to the invention has low power consumption and a biologically based nature and may be used to regulate breathing, heart beat and other rhythmic movements. An implantable neural surrogate according to the invention also may be provided to adapt itself to optimize its own efficiency and that of the biological systems it controls.

The invention also may be used in miniature systems to modulate repetitive cyclical movements based on sensory feedback, such as miniature walking, running, flapping, flying and swimming machines. Ultra-small, adaptable control systems are preferred for such robots, for various reasons (such as providing an obtrusive device or to fit into a limited space). The present invention can provide such control systems. Miniature robots and robotics systems may be used for reconnaissance, and search missions (such as in a fallen building after an earthquake), and will benefit from a compact control system according to the present invention. Also, miniature embodiments of the present invention may be used in surgical applications, such as a catheter provided with a miniature CPG chip controlling how the catheter contacts and wiggles as it "swims" in blood.

In other embodiments, the invention may be used in toy applications, such as a toy animal comprising a controller according to the invention. Because the invention can provide a controller that is relatively small and low power, the controller can be mounted directly on toy robot limbs to be controlled. In addition, its low power nature means that it will not drain the batteries quickly. The adaptive aspect means that the toy robot animal (such as a "Tabby" cat) can change its gait based on the obstacles and type of environment in which it is walking, without using any CPU, using controls that are biologically inspired, and using a distributed network of autonomous controllers that are coupled through the dynamics of the toy robot and the properties of the environment.

EXAMPLE NO. 1

A robot comprising a biomorphic leg was constructed using a neuromorphic chip on which CPGs were modeled as distributed systems of non-linear oscillators. To provide basic coordination in a leg, two neurons were phasically coupled together to achieve oscillations. They were coupled together to be alternatively active, with the alternating activity as the basic coordination that drove the hip of the robot. A phase control circuit governed the phase difference between the neurons. The oscillator neurons drove two integrate-and-fire spiking motoneurons, which drove an actuator. (The spiking neuron could also drive biological muscle or it could also be used to drive a pneumatic cylinder, a McKibben actuator or biomuscle directly).

The robot used servomotors to provide electrical power. To be compatible with this technology, low-pass filters 14 were applied to the spiking neurons and the resulting smooth graded velocity signal was integrated.

The circuit was used in autonomous operation and with sensory feedback from stretch receptors used to adjust the CPG. Properties of the constructed biomorphic leg were demonstrated. The biomorphic limb and its control circuit produced stable rhythmic motion, and also compensated for intentional biases in the chip as well as mechanical complexity of an active hip and passive knee.

As basic components of the robot, neurons and a CPG chip were used with a robotic leg.

Neurons

The neuron used was an integrate-and-fire model. A capacitor, representing the membrane capacitance of biological neurons, integrated impinging charge. As seen with reference to FIG. 2, the capacitor was set that when the "membrane-potential" exceeds the threshold of a hysteretic comparator 5a, the neuron output is high. In this circuit, this logic high triggers a strong discharge current that adjusts the membrane potential to below the threshold of the comparator, thus causing the neuron output to adjust. This circuit therefore emulated the slow phase and fast phase dynamics of real neurons, with the process then starting anew. FIG. 2 shows a schematic of the neuron circuit used in the robot of Example 1.

The neurons used in Example 1 were those that carry activation information in the frequency of spikes. The rate at which the membrane potential charges up controls the firing frequency of the neuron. This rate is given by the sum of the total charge flowing in and out of the membrane capacitance.

The strength of the reset current source determines the width of each neural spike. The discharge current is usually set to a large value so that each spike is narrow and is not influenced by the charge injected onto the membrane capacitor. Typically, the neuron is set to fire at a nominal rate at rest, with additional input increasing or decreasing the firing rate, and with shunting inhibition that can also silence the neuron.

The following equation (1) gives the dynamic equation for the neuron in Example 1.

$$C_i^{mem} \frac{dV_i^{mem}}{dt} = I_{spon} - S_i I_{dis} + \sum_j S_j I_j^+ - \sum_j \overline{S}_j I_j^- \quad (a) \quad (1)$$

$$S_i = \begin{cases} 1 & \text{if } V_i^{mem} > V_T^+ \\ 0 & \text{if } V_i^{mem} < V_T^- \end{cases} \quad (b)$$

With reference to equation (1), there are three input voltages: (1) a feedback input from a hysteretic comparator ($S_i$), (2) Excitatory inputs from other neurons ($S_j$) and (3) Inhibitory Inputs from other neurons ($\overline{S}_j$). These inputs are weighted by current sources. These current sources are denoted $I_{dis}$, $I_j$ and $\overline{I}_j$ respectively. In addition, a constant current injection sets a spontaneous spike rate of the neuron. As noted above, $I_{dis}$ sets the spike duration. Finally, the term $V_T^+$ and $V_T^-$ set the thresholds for the hysteretic comparator respectively.

The spike trains impinging on a neuron activate switches that allow charge quanta to flow into or off the membrane capacitor. The amount of charge transferred per spike is the synaptic weight and is controlled by an applied voltage that regulates the current sources. Modulation of this voltage allows the adaptation of the neural firing rate and is used during learning. The left-hand side of FIG. 2 shows the schematic of the synapse 12, while equation (1) above shows how the neuron is affected by the synaptic weight.

In addition to spiking neurons, neurons with graded response also were used in making the robot of Example 1. The graded-response neurons were essentially the same as the spiking neuron except for replacing the hysteretic comparator with a linear amplifier stage and not using feedback voltage.

Oscillators on the CPG Chip

The neural circuits for creating the CPG were constructed using cross-coupled square-wave oscillators, with the output of these oscillators driving the bursting motoneurons described above. A master-slave configuration of the neurons was used, to allow construction of an oscillator with a constant phase relationship. By setting the excitatory and inhibitory weights to equal values, a square-wave with a duty-cycle of 50% was obtained. The phase relationship between the two sides was subject to being varied. The frequency of oscillation was set by the magnitude of the weights. This asymmetrically cross-coupled oscillator served as the basic CPG unit, with the oscillator subject to being modified according to the application so that if a different application was desired later, the oscillator could be reset. By injecting or removing charge from the membrane capacitors of the oscillator neurons, the properties of the CPG could be altered.

To be able to produce more complex waveforms, a phase controller was included on the chip. This phase controller allows the phase difference between oscillators to be set arbitrarily. For the experiments described herein, a strict 180 degrees phase relationship was needed, hence, an inverted version of an oscillator was used, as shown in FIG. 3.

Neural Circuit on the CPG Chip

The complete neural circuit as used in making the robot of Example 1 is shown in FIG. 3. The output of the basic oscillator unit 13 was used to inhibit the firing of the spiking motoneuron. The oscillator 13 was set so that when the oscillator output is high, the motoneuron is not allowed to fire, which produces two streams of 180 degrees out of phase spike trains. These trains could be low-pass filtered to get a voltage which could be interpreted as a motor velocity. Consequently, the oscillator controlled the length of the motor spike train, while the spike frequency indicated the motor velocity. The spike frequency was regulated by a feedback loop. Spiking placed charges on the neuron membrane capacitor seen in the lower part of FIG. 3. The integrated charges were buffered and then used to down regulate spike frequency. In this way spike frequency was less sensitive to component variations.

Four neurons were provided as described above, in the form of a custom VLSI CPG chip occupying less than 0.4 square mm.

Robotic Leg

In assembling the self-adaptive robotic leg of Example 1, a robotic leg that was a small (10-cm height) two-joint mechanism was combined with the above-mentioned CPG chip via components to interface the chip to the robotic leg, and a data collection facility. In the robot of Example 1, only the "hip" was driven with the "knee" being completely passive and swinging freely, rotating on a low friction ball-bearing joint. A hard mechanical stop prevented the knee from hyper-extending.

In Example 1, the neurons of the CPG chip were interfaced to a servomotor using a rudimentary muscle model. The muscle dynamics were simulated as a low pass filter to smooth the output of the spiking neurons. This was followed by an integrator, implemented in software, to convert the velocity signal to a position command needed by the servomotor. A bias (intended to be typical of uncompensated parameters in a chip) was intentionally introduced into the chip to cause an asymmetry in the backward and forward swing of the leg.

The robotic leg of Example 1 was provided with three sensors. Two LVDT sensors monitored the position of the knee and hip joints. LVDT sensors were used because they introduced minimal friction and had infinite resolution. Additionally, the robot was provided with a miniature load-cell sensor that monitored ground forces. The units of the load cell are uncalibrated in all figures.

EXPERIMENTATION

Using the inventive robot of Example 1, two additional sensory mediated loops that adapt the oscillator and the motoneuron spiking were added, and testing relating to sensory adaptation and learning was performed. The inventive circuit used in the experimentation was one consuming less than one microwatt of power and occupying less than 0.4 square millimeters of chip area.

Adaptation-based "Stretch Receptor"

As shown in FIG. 3, the oscillator neurons of the robot of Example 1 could be stopped or started with direct inhibitory and excitatory sensory inputs, respectively. When the inputs were received as strong inhibition, the membrane capacitor was shunted and discharged completely. It remained in this state until the inhibition was released, then the normal dynamics of the oscillator continued from the inactive state. On the other hand, if the sensory input was received as a strong excitation, the oscillator was driven into an active state. When the excitation was released, the oscillator continued from the active state. The charge-up or discharge of the membrane capacitor was influenced by any direct sensory input. For periodic sensory inputs, the oscillator outputs could be driven such that they phase locked to the inputs. Thus the oscillator was entrained to the dynamics of the system under control.

This property of the oscillator being entrained to the dynamics of the system under control was used to mimic the effect of the stretch reflex in animals. When the leg of an animal is moved to an extreme position, a special sensor called a stretch receptor sends a signal to the animal's CPG causing a phase adjustment. This biological phase adjustment response is mimicked in the circuit of Example 1. Referring to FIG. 3, the biomorphic leg of Example 1 may reach an extreme position while still being driven by the oscillator. In this case, virtual position sensors 16, which mimic stretch receptors, send a signal to ResetA 15a or ResetB 15b to cause an adjustment of the oscillator circuit as appropriate to cause a hip joint velocity reversal.

Spike Frequency Adaptation

To provide learning, the chip included a short-term (on the order of seconds) analog memory to store a learned weight. This architecture favors a continuous leaning rule. Spikes from the motoneurons were used to increase or decrease a voltage on a capacitor; the voltage was used to set the connection weight of another neuron. In the absence of the training inputs, the stored weights decay at approximately 0.1V/s. FIG. 3 shows a schematic for adapting the spiking frequency of the motoneurons based on the swing amplitude of the limb.

In FIG. 3, the limb was driven back and forth with a velocity signal that was obtained by low-pass filtering the activity of the motoneurons. Because the CPG oscillator fixed the duration of the spike train, changing the spiking frequency of the motoneuron altered the amplitude of the velocity signals, which in turn varied the swing amplitude of the limb. If the amplitude of swing did not reach the maximum positions, the motoneuron spike rate was increased. An increase in spike rate was kept bounded by negative feedback to the learning circuit. When the swing amplitude reached maximum, the positive input to the learning circuit was reduced, thus allowing the spiking rate to settle to a constant value. The continuous negative feedback of the spike rate and the input from the position detectors maintained the learned spiking rate. The duration of the burst component of the spike train was further controlled by feeding the position signals directly to the CPG oscillators to reverse the trajectory of motion at the end points. This allowed very asymmetric forward and backward velocity signals to be adaptively re-centered.

Set-up

The small robotic leg of Example 1 was used for the experimental set-up. The output of the hip LVDT was sampled digitally. The signal was interval coded. Two intervals were selected as representing the extremes of movement of the hip (called "virtual position sensor" in FIG. 3). When these extremes were reached, the corresponding interval was active. This interval then sent a signal to the CPG chip causing an appropriate adjustment.

An oscillator frequency was selected by hand to be approximately 2–3 Hz. This frequency would excite the mechanical structure and cause the leg to "run" a rotating drum. In practice the leg was not highly sensitive to this excitation frequency but no effort was made to quantify this sensitivity.

Experiment 1

Running with a Passive Knee

With Example 1 in the above experimental setup, the CPG circuit was set to drive the actuator in the hip joint. The knee joint was passive and rotated with very little friction. The assembly was suspended above a rotating drum. The CPG circuit was started, and data was collected for three sensors, including foot pressure, knee and hip. "Stretch receptor" sensory feedback from the hip was used as feedback to the CPG.

Running with the passive knee included a notable result that in the system of Example 1 according to the present invention, the knee joint adapted the correct dynamics to enable running. As the upper limb swung forward, the lower limb rotated so that the foot came off the ground. When the upper limb was suddenly accelerated backward, the momentum in the lower limb forced the knee to lock in place. At just the correct moment, the foot contacted the ground and the subsequent loading kept the knee joint locked in place. As the foot traveled backward it eventually began to unload. Stored energy in the elastic foot caused it to "kick up" and smartly snap off the ground, an effect most noticeable at higher velocities.

Figure 4:
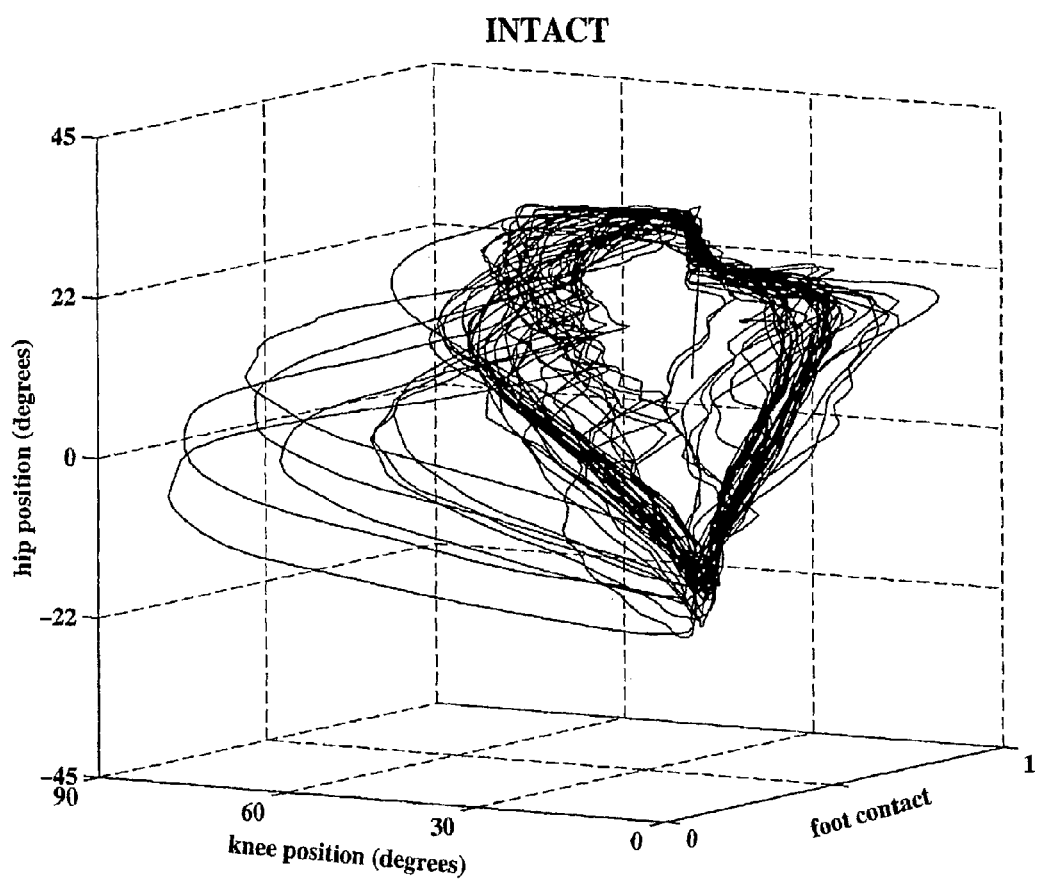
FIG. 4 is a hip, knee and foot-contact phase diagram for a representative embodiment according to the invention.

FIG. 4 shows a phase plot of the knee, foot and hip position and foot contact for the robot of Example b 1 when Experiment 1 was performed. In FIG. 4, most of the trajectory is in a tight bundle, while the outlying trajectories represent perturbations. The bulk of the trajectory describes a tight 'spinning top' shaped trajectory while the few outlying trajectories are caused by disturbances. After a disturbance the trajectory quickly returns to its nominal orbit, which reflects that the system was stable.

Experiment 2

Sensory Feedback Lesioning

Experiment 1 was repeated except for lesioning (turning off) sensor feedback periodically. Data was collected as in Experiment 1.

Figure 5:
FIG. 5 is a series of graphs, for a hip, knee, and foot, showing the effect of lesioning sensory feedback when the invention is used.

FIG. 5 shows the effect of lesioning sensory feedback on the position of the hip and knee joints as well as the tactile input to the foot. After lesioning the leg drifted backward significantly due to a bias built into the chip. When the sensory input was restored, the leg returned to a stable gait. When the feedback was lesioned (Time 11–19 seconds and 31–42 seconds), the hip drove backward significantly. As it did the foot began to lose contact with the surface and the knee stopped moving. When the lesion was reversed at 19 and 42 seconds, the regularity of the gait was restored.

Figure 6A:
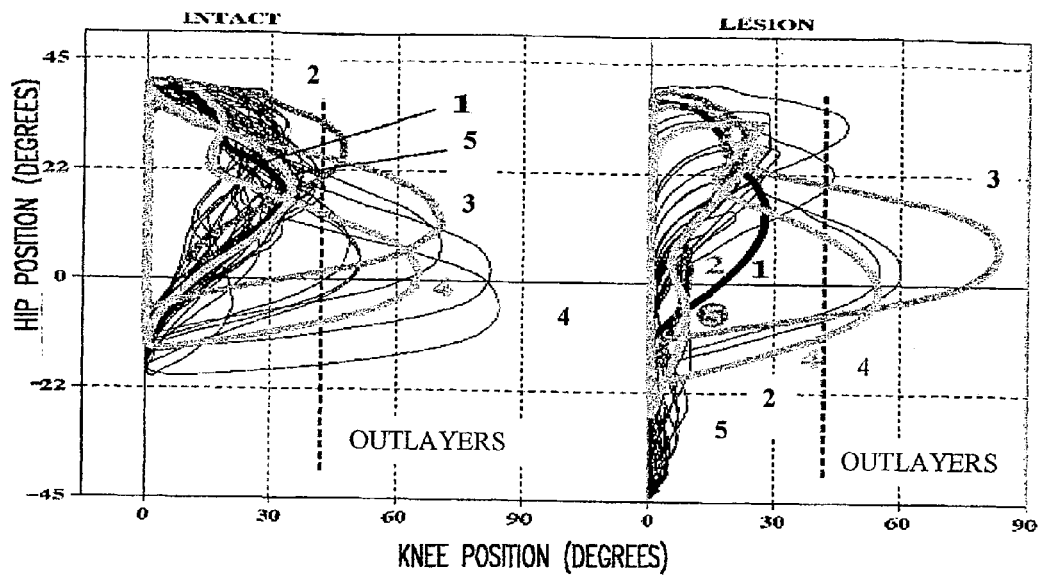
FIGS. 6(a) and 6(b) are plots of hip position versus time for a robot according to the present invention.
Figure 6B:
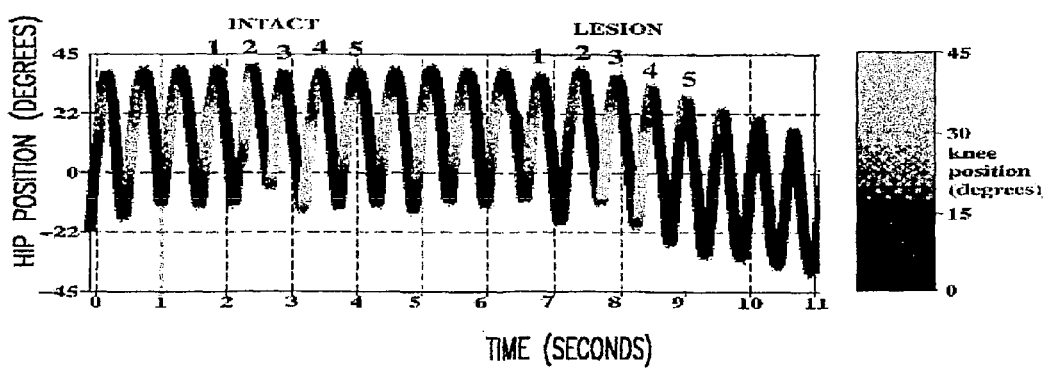

FIGS. 6(A) and (B) show the effect of perturbations on gait with intact and lesioned sensory feedback. In FIG. 6(A), five sequential trajectories (numbered) in intact and lesioned conditions are represented as ranging between black and light gray. A perturbation at 2 in the intact case lead initially to worse trajectories (3 and 4), but quickly stabilized to the nominal orbit (5). In the lesioned case, chip bias caused a perturbation at 2 from which the gait could not recover; the hip was forced backward (3,4, and 5). In FIG. 6(B), the same ten trajectories shown in FIG. 6(A) are presented as hip positions through time, with various knee positions numbered. Intact sensory feedback permitted recovery while lesioning caused drift of both the hip and knee.

The experimentation provided the following information about gait stability for the robot of Example 1. Perturbations to the leg caused momentary disturbances. As seen in FIG. 4, several of the trajectories are clear "outlyers" to the typical orbit, and resulted from environmental disturbances. It was found that sensory feedback could compensate for both the bias of the chip and environmental perturbations. FIGS. 6(A) and (B) show restoration to a nominal orbit after perturbation in intact and lesioned cases. In the intact case, aperturbation at cycle '2' lead to outlying trajectories, but the trajectory was quickly restored to the nominal orbit. In the lesioned case, removal of sensory feedback caused the chip bias to destroy the trajectory of the leg. The gait quickly deteriorated.

Thus, the present inventors have provided what they believe to be the first experimental results of an adaptive VLSI neural chip controlling a robotic leg. Using sensory feedback, the circuit adapted the gait of the leg to compensate both for chip bias and environmental perturbations. This work represents the first experimental results known to the present inventors of an adaptive VLSI neural chip controlling a robot leg. The experimentation set forth herein establishes a successful working hardware implementation of a CPG-based model according to the invention. The data of FIGS. 4, 5 and 6 establish that a VLSI chip according to the invention having only 4 neurons and occupying less than 0.4 square nm controlled a leg running on a treadmill.

The data also reflect success in providing running as a dynamic process, for the under-actuated robotic leg of Example 1. In the results presented here, the energy injected into the hip was sufficient to excite an orbital trajectory of the knee as well. The hip, knee, and foot sensor orbit appear remarkably stable when the CPG circuit was stabilized using sensory feedback. The data of FIGS. 4, 5 and 6 reflect that control of a running leg using a VLSI CPG chip. The data further reflect successful application of a neuromorphic approach to build a complete artificial nervous system to control a robot. The functioning of the robot of Example 1 confirmed the implementation of an adaptive CPG model in a compact analog VLSI circuit. The experimentation confirms that the circuit in use has adaptive properties that allow it to tune its behavior based on sensory feedback. The adaptive CPG chip according to the present invention is thought to be the first functioning adaptive CPG chip. The results of the experimentation suggest that inexpensive, low power and compact controllers for walking, flying and swimming machines and other movement machines may be constructed using the present invention.

Also, the experimentation confirms that the invention provides a functioning chip, based on principles of the locomotor-control circuits in the nervous system, that mimics many of the features of a biological CPG. A circuit according to the invention was shown to control a robotics leg running on a circular treadmill. Furthermore, a circuit according to the invention was shown to use sensory feedback to stabilize the rhythmic movements of the leg The experimentation confirms that the invention may provide inexpensive circuits that are adaptable, controllable and able to generate complex, coordinated movements. The experimentation establishes that the present invention provides self-adaptation in a CPG-based system based on sensory input.

While the invention has been described in terms of its preferred embodiments, those skilled in the art will recognize that the invention can be practiced with modification within the spirit and scope of the appended claims.

We claim:

1. A central pattern generator-based system for controlling at least one mechanical limb, comprising
   at least one mechanical limb;
   a system for phase adjustment of the central pattern generator based on a sensory trigger in or derived from sensory feedback; and
   a non-biological central pattern generator that autonomously generates a rhythmic pattern of commands for controlling repetitive cyclical movement of the at least one mechanical limb wherein said commands and said rhythmic pattern of commands are adapted as a function of sensory feedback.

2. The central pattern generator-based system of claim 1, wherein:
   said system for phase adjustment of the central pattern generator being based on
   at least one sensory trigger in or derived from sensory feedback; and
   a system for controlling firing frequency of motoneurons as a function of the sensory feedback or the sensory trigger.

3. The central pattern generator-based system of claim 1, further including at least one memory device.

4. The central pattern generator-based system of claim 3, wherein the memory device controls adaptation of output from the central pattern generator.

5. The central pattern generator-based system of claim 4, wherein the output includes integrate-and-fire neurons.

6. The central pattern generator-based system of claim 1, wherein the system is at least one chip.

7. The central pattern generator-based system of claim 6, including at least one chip containing electronic analogues of biological neurons, synapses and time-constraints.

8. The central pattern generator-based system of claim 6, including at least one chip that includes dynamic memories and phase modulators.

9. The central pattern generator-based system of claim 6, wherein the system includes at least one chip in which components are integrated with hardwired or programmable circuits.

10. The central pattern generator-based system of claim 1, wherein the central pattern generator is a distributed system of at least two non-linear oscillators.

11. The central pattern generator-based system of claim 10, wherein the distributed system includes at least one neuron phasically coupled to a neuron or a sensory input.

12. The central pattern generator-based system of claim 10, wherein the distributed system includes at least two neurons phasically coupled to each other, to another neuron, or to a sensory input.

13. The central pattern generator-based system of claim 12, wherein phasic coupling is in-phase, 180 degrees out of phase, or any number of degrees out of phase.

14. The central pattern generator-based system of claim 12, wherein phasic coupling is based on rhythmic movement application.

15. The central pattern generator-based system of claim 12, including a phase control circuit.

16. The central pattern generator-based system of claim 12, including at least one integrate-and-fire spiking motoneuron driven by the phasically coupled neurons.

17. The central pattern generator-based system of claim 6, wherein the system includes a central pattern generator chip and at least one biological neuron.

18. The central pattern generator-based system of claim 17, including multiple chips.

19. The central pattern generator-based system of claim 1, including at least one muscle.

20. The central pattern generator-based system of claim 1, wherein the system is a robot.

21. The central pattern generator-based system of claim 1, including at least one sensor for collecting sensory feedback.

22. The central pattern generator system of claim 21, including a system for phase adjustment of the central pattern generator based on at least one sensory trigger in the received sensory feedback.

23. The central pattern generator-based system of claim 1, wherein the sensory feedback is received from the at least one mechanical limb.

24. The central pattern generator-based system of claim 1, wherein the sensory feedback is received from a sensing modality.

25. A central pattern generator-based system for controlling at least one mechanical limb, comprising
    at least one mechanical limb; and
    a non-biological central pattern generator that autonomously generates a rhythmic pattern of commands for controlling repetitive cyclical movement of the at least one mechanical limb wherein said commands and said rhythmic pattern of commands are adapted as a function of sensory feedback
    wherein the system is a non-linear oscillator including electronic analogues of biological neurons, synapses and time-constraints, dynamic memories and phase modulators.

26. A central pattern generator-based system for controlling a biological system for rhythmic movement, comprising
    an interface with a biological system that can provide sensory feedback from said biological system;
    a system for phase adjustment of the central pattern generator based on a sensory trigger in or derived from sensory feedback; and
    a non-biological central pattern generator that autonomously generates a rhythmic pattern of commands for controlling repetitive cyclical movements of the biological system wherein said commands and said rhythmic pattern of commands are adapted as a function of sensory feedback.

27. The central pattern generator-based system of claim 26, further including at least one memory device.

28. The central pattern generator-based system of claim 27, wherein the memory device controls adaptation of output from the central pattern generator.

29. The central pattern generator-based system of claim 28, wherein the output includes integrate-and-fire neurons.

30. The central pattern generator-based system of claim 26, wherein the system is at least one chip.

31. The central pattern generator-based system of claim 30, including at least one chip containing electronic analogues of biological neurons, synapses and time-constraints.

32. The central pattern generator-based system of claim 30, including at least one chip that includes dynamic memories and phase modulators.

33. The central pattern generator-based system of claim 30, wherein the system includes at least one chip in which components are integrated with hardwired or programmable circuits.

34. The central pattern generator-based system of claim 30, wherein the system includes a central pattern generator chip and at least one biological neuron.

35. The central pattern generator-based system of claim 34, including multiple chips.

36. The central pattern generator-based system of claim 26, wherein the central pattern generator is a distributed system of at least two non-linear oscillators.

37. The central pattern generator-based system of claim 36, wherein the distributed system includes at least one neuron phasically coupled to a neuron or a sensory input.

38. The central pattern generator-based system of claim 36, wherein the distributed system includes at least two neurons phasically coupled to each other, to another neuron, or to a sensory input.

39. The central pattern generator-based system of claim 38, wherein phasic coupling is in-phase, 180 degrees out of phase, or any number of degrees out of phase.

40. The central pattern generator-based system of claim 38, wherein phasic coupling is based on rhythmic movement application.

41. The central pattern generator-based system of claim 38, including a phase control circuit.

42. The central pattern generator-based system of claim 38, including at least one integrate-and-fire spiking motoneuron driven by the phasically coupled neurons.

43. The central pattern generator-based system of claim 26, including at least one muscle.

44. The central pattern generator-based system of claim 26, including at least one sensor for collecting sensory feedback.

45. The central pattern generator system of claim 44, including a system for phase adjustment of the central pattern generator based on at least one sensory trigger in the received sensory feedback.

46. The central pattern generator-based system of claim 26, wherein the sensory feedback is received from the at least one biological limb.

47. The central pattern generator-based system of claim 26, wherein the sensory feedback is received from a sensing modality.

48. A central pattern generator-based system for controlling a biological system for rhythmic movement, comprising
an interface with a biological system that can provide sensory feedback from said biological system;
a non-biological central pattern generator that autonomously generates a rhythmic pattern of commands for controlling repetitive cyclical movements of the biological system wherein said commands and said rhythmic pattern of commands are adapted as a function of sensory feedback;
a system for phase adjustment of the central pattern generator based on at least one sensory trigger in or derived from sensory feedback; and
a system for controlling firing frequency of motoneurons as a function of the sensory feedback or the sensory trigger.

49. A central pattern generator-based system for controlling a biological system for rhythmic movement, comprising
an interface with a biological system that can provide sensory feedback from said biological system;
a non-biological central pattern generator that autonomously generates a rhythmic pattern of commands for controlling repetitive cyclical movements of the biological system wherein said commands and said rhythmic pattern of commands are adapted as a function of sensory feedback;
wherein the system is a non-linear oscillator including electronic analogues of biological neurons, synapses and time-constraints, dynamic memories and phase modulators.

50. A method for controlling a mechanical or biological system for rhythmic movement, comprising:
(A) measuring sensory feedback to obtain measured sensory feedback;
(B) processing the measured sensory feedback to obtain data for a plurality of designated parameters; and
(C) via a central pattern generator-based system, applying a set of rules to the obtained data to generate at least one signal for commanding the limb or biological system for rhythmic movement, wherein the central pattern generator-based system comprises a circuit that mimics a biological central pattern generator.

51. The method of claim 50, including (D) via the central pattern generator-based system, applying the generated signal to command the limb or biological system for rhythmic movement.

52. The method of claim 50, wherein the central pattern generator system comprises a circuit comprising at least two coupled non-linear oscillators.

53. The central pattern-based system as recited in claim 26, including at least one mechanical limb.

54. The autonomous device of claim 53 wherein the limb is a leg, arm, wing or appendage for swimming.

55. The movement device of claim 53 including at least two limbs.

56. The central pattern-based system as recited in claim 26, wherein the system is a breathing controller.

57. The central pattern-based system as recited in claim 26, wherein the system is a pacemaker.

58. The central pattern-based system as recited in claim 26, wherein the system is a running device.

59. A method for modifying a continuous waveform provided by a non-biological central pattern generator, comprising the steps of:
(A) provision of a continuous waveform by a non-biological central pattern generator;
(B) provision of sensory feedback to the non-biological central pattern generator;
(C) rule-application by the non-biological central pattern generator to the sensory feedback;
(D) based on the rule-application, determination by the non-biological central pattern generator to modify or maintain the continuous wave form.

60. The method of claim 59, wherein the non-biological central pattern generator modifies the wave form.

61. The method of claim 59, wherein the rule-application is the application of adaptive ring rules.

* * * * *